US009050099B2

(12) United States Patent
Miersch

(10) Patent No.: US 9,050,099 B2
(45) Date of Patent: Jun. 9, 2015

(54) SURGICAL JAW INSTRUMENT HAVING A SLIDE SYSTEM

(75) Inventor: Hannes Miersch, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 804 days.

(21) Appl. No.: 13/381,413

(22) PCT Filed: Jun. 10, 2010

(86) PCT No.: PCT/EP2010/003470
§ 371 (c)(1), (2), (4) Date: Dec. 29, 2011

(87) PCT Pub. No.: WO2011/000465
PCT Pub. Date: Jan. 6, 2011

(65) Prior Publication Data

US 2012/0101484 A1 Apr. 26, 2012

(30) Foreign Application Priority Data

Jul. 1, 2009 (DE) ......................... 10 2009 031 424

(51) Int. Cl.
*A61B 18/14* (2006.01)
*A61B 17/29* (2006.01)
*A61B 18/00* (2006.01)

(52) U.S. Cl.
CPC ............. *A61B 18/1445* (2013.01); *A61B 17/29* (2013.01); *A61B 2017/2933* (2013.01); *A61B 2017/2936* (2013.01); *A61B 2018/00083* (2013.01)

(58) Field of Classification Search
USPC ..................................... 606/51, 52, 205–207
See application file for complete search history.

(56) References Cited

U.S. PATENT DOCUMENTS

| | | | | |
|---|---|---|---|---|
| 4,819,633 | A | 4/1989 | Bauer et al. | |
| 5,395,369 | A * | 3/1995 | McBrayer et al. | 606/51 |
| 5,697,949 | A * | 12/1997 | Giurtino et al. | 606/205 |
| 5,766,170 | A * | 6/1998 | Eggers | 606/48 |
| 5,849,022 | A * | 12/1998 | Sakashita et al. | 606/174 |
| 6,190,386 | B1 | 2/2001 | Rydell | |
| 6,361,534 | B1 * | 3/2002 | Chen et al. | 606/45 |
| 7,628,792 | B2 * | 12/2009 | Guerra | 606/51 |
| 8,568,443 | B1 * | 10/2013 | Jackman et al. | 606/205 |
| 2005/0090817 | A1 * | 4/2005 | Phan | 606/41 |
| 2009/0131932 | A1 | 5/2009 | Vakharia et al. | |

FOREIGN PATENT DOCUMENTS

| | | |
|---|---|---|
| DE | 201 21 161 U1 | 5/2002 |
| WO | WO 96/27338 | 9/1996 |

OTHER PUBLICATIONS

Jan. 17, 2012 International Preliminary Report on Patentability issued in PCT/EP2010/003470 w/translation.

* cited by examiner

*Primary Examiner* — Michael Peffley
(74) *Attorney, Agent, or Firm* — Oliff PLC

(57) ABSTRACT

A surgical jaw instrument having two jaw pieces mounted at the distal end section of a shaft for relative reciprocal displacement, whereby at each displaced jaw piece a sliding rod is fastened at an incline to the axis of the shaft, to which a displaceable sliding element can be connected parallel to the axis of the shaft in such a way that upon displacement of the sliding element, the jaw pieces are relatively reciprocally displaced wherein a second sliding element is mounted at the first sliding element, diametrically opposed relative to the sliding rod.

9 Claims, 1 Drawing Sheet

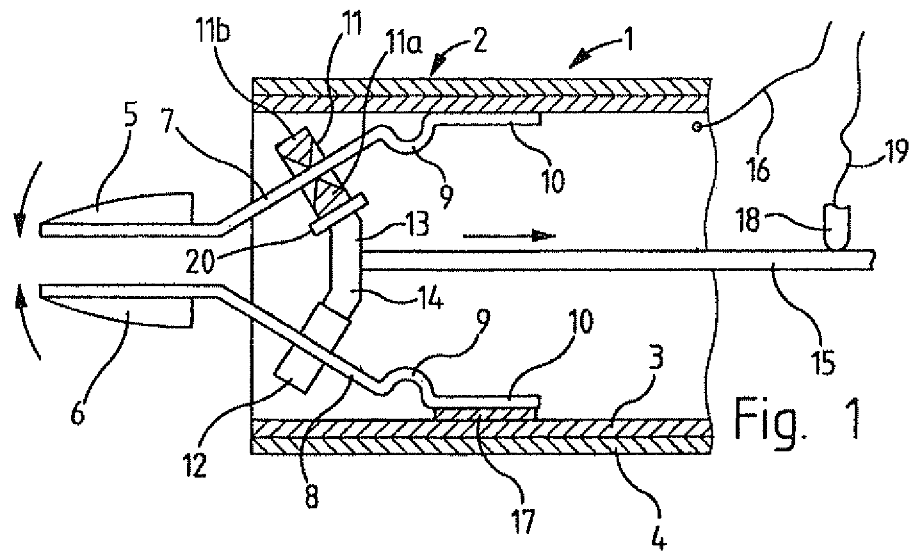
21b
21
7
21a
Fig. 2
13
31
31b
32
7
Fig. 3
32
31a
13
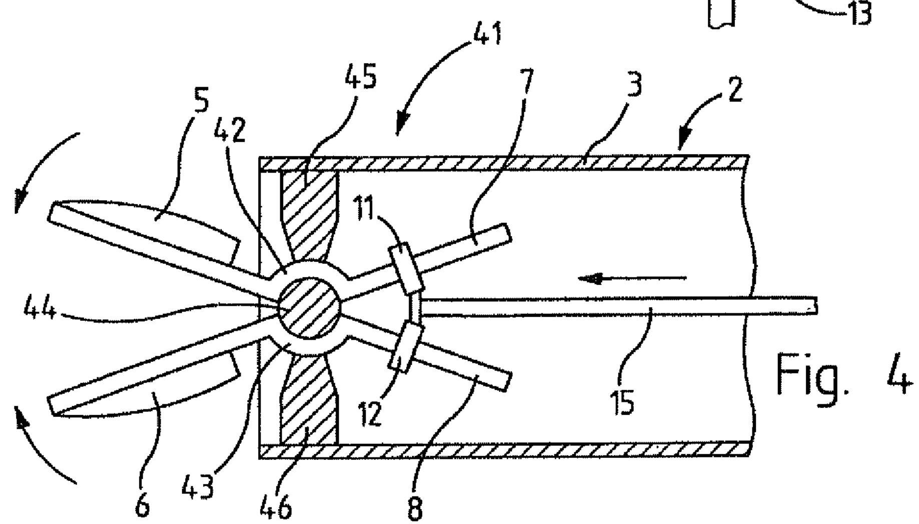

SURGICAL JAW INSTRUMENT HAVING A SLIDE SYSTEM

BACKGROUND OF THE INVENTION

I. Field of the Invention

The invention relates to a surgical jaw instrument.

II. Description of the Related Art

Jaw instruments of this type are known, for example, from U.S. Pat. No. 6,190,386 B1 and U.S. Pat. No. 4,819,633 A. In both designs, the sliding rods are located diverging in distal direction. The distal edge of a thrust tube that can be displaced in the axial direction of the shaft is the sliding element.

The advantage of this known solution lies in the special simplicity of the design, whereby in particular, the complicated joint between the jaw components is avoided, as it is used in most forceps designs and scissors designs. This also results in an additional important advantage, namely, the simpler electric isolation for forceps provided with electrodes that are used, for example, for vascular electrocoagulation. In particular, in the case of bipolar design, i.e. with different terminals at the two jaw components of a forceps or a scissors, enormous technical problems arise at the joints between the jaw components with respect to the electric isolation. These are completely avoided by using the design cited at the beginning.

SUMMARY

The known design that was cited at the beginning has, however, also a significant disadvantage. Such a forceps or scissors is customarily constructed in such a way that it closes the jaw pieces upon a displacement of the thrust tube. This can take place with a high degree of force. But the reverse motion, namely the opening motion of the jaw pieces cannot take place by an actuation of the thrust tube. In known designs, this displacement is generated by using a spring. In the known designs, the sliding rods are designed as flat springs for this purpose. But the resilient forces of this design must be small, as they must be continually overcome for closing with the thrust tube. It generates only small potential opening forces, which is very disruptive in some applications, for example, when widening or any kind of separating pressure motions are to be performed with such a forceps or scissors. If such tasks are to be performed with a sufficient level of force, a special jaw instrument must be used that can perform the opening motion with a high degree of force by using kinematic inversion.

The objective of the present invention consists of expanding the possibilities of application for a surgical jaw instrument of the type cited at the beginning.

According to embodiments of the invention, a sliding rod displacing a jaw piece does not only abut on a sliding element on one side, as is known from prior art, but also on a second sliding element on the opposite side of the sliding rod. The sliding elements are fastened to each other. If the sliding elements are displaced in one direction, the jaw instrument is closed, and if they are displaced in the other direction, the jaw instrument is opened. Both functions are possible by using the same high degree of force that can be exerted upon a sliding element. The required design changes compared with a known design in prior art are relatively small. Therefore, at low cost, the applicability of a forceps or a scissors can be increased significantly, as it can not only be operated with a high degree of closing force, but also with a high degree of opening force. Thus, with a jaw instrument, both operating modes are possible with a high degree of force. The customary variants of jaw instruments are possible; these are, for example, those with only one moving and one rigid jaw piece, or those with two displaced jaw pieces. The jaw instrument can, depending on the design of the jaw pieces, be provided as forceps or as scissors, and can be designed with a longer shaft, for example, for laparoscopic surgeries.

A sliding rod having the design according to the invention can, as is the case in the designs cited at the beginning, be mounted at a connecting rod located in the shaft tube. Advantageously, however, the sliding rod is mounted on the shaft tube. Thereby, this mounting is designed as a joint, in order to make the angular motion of the sliding rod possible while it is gliding. Thereby, it is advantageous that the joint is designed as bendable part of the sliding rod, which makes a particularly simple construction possible, in particular then, when the sliding rod is used as a conductor.

In this type of construction, all displaceable jaw parts are mounted at the end of the sliding rod that is located diametrically opposed to the joint, they are thus moved as one-armed levers. In the crowded cross section of a laparoscopic jaw instrument, this severely limits the angle of deflection and thus the angle of aperture of a forceps or scissors. Hereby, the sliding rod and jaw part are connected by a bearing part, which is mounted on the shaft. Sliding rod and jaw part thus form a two-armed lever that is mounted in the center, with which a larger angular deflection is possible in the limited space.

It is thereby advantageous that the bearing position is designed as groove mounting that can not only absorb extremely high forces, but also makes a better electric isolation possible of gliding rod and jaw piece.

Preferably, at least one of the jaw pieces has an electrode. With it, the jaw instrument can be used, for example, for coagulation, whereby preferably, of course, both jaw pieces are connected bipolar, the connection of one jaw piece takes place via the shaft, and the connection of the other jaw piece is established by a connecting rod that drives the sliding elements. Thus, design elements that are already present anyway, which extend over the length of the shaft and consist of electrically conductive metal are used as terminal leads, which significantly simplifies the design.

BRIEF DESCRIPTION OF THE DRAWINGS

The drawing illustrates embodiments of the invention schematically and by way of example. Shown are:

FIG. 1 shows an axial section through the distal end section of a jaw instrument according to the invention with two sliding members;

FIG. 2 shows a sliding member according to FIG. 1 in a design variant;

FIG. 3 shows a sliding member according to FIG. 1 in an additional design variant; and FIG. 4 shows an illustration according to FIG. 1 of a jaw instrument in a design variant.

DETAILED DESCRIPTION OF EXEMPLARY EMBODIMENTS

FIG. 1 shows a surgical jaw instrument 1 with a shaft 2 that consists of a metal tube 3 with an isolating covering 4.

Two jaw pieces 5, 6 are located projecting over the distal end of shaft 2, that are mounted at the distal ends of two sliding rods 7, 8 that are converging slanted in distal direction. The proximal ends of the sliding rods are fastened articulated with joints 9 at end pieces 10, which are mounted at metal tube 3.

Joints 9 allow a deviating motion of sliding rods 7, 8. Joints 9 can, for example, be designed as hinged joints with bearing pin, in the preferred embodiment shown in FIG. 1, however, they are designed as bendable spring elements that make an integral connection between jaw pieces 5, 6 and end pieces 10 possible.

Sliding members 11, 12 engage with sliding rods 7, 8, of which sliding member 11 is shown in cross section in FIG. 1. Both sliding members 11, 12 can be designed identically. As can be seen on sliding element 11, it has two sliding elements 11*a*, 11*b* that are designed as blade edges in this exemplary embodiment, having a gap in between, in which sliding rod 7 is retained slideable. With its two sliding elements 11*a*, 11*b*, sliding member 11 engages at the two sides that lie against sliding rod 7 in the plane of projection, and it can be displaced extending along sliding rod 7. Sliding member 12 is designed exactly alike and mounted on sliding rod 8.

Both sliding members 11, 12 are mounted via cross pieces 13 and 14 at a connecting rod 15. If the connecting rod is pulled back in proximal direction in shaft 2, then as a result of the sliding adjustment of the sliding members 11, 12 on sliding rods 7, 8, sliding rods 7, 8 are deviated toward each other and with them jaw pieces 5, 6, as it is shown by the arrows indicating the closing motion.

To bring about the closing motion that was described, sliding members 11, 12 are displaced in proximal direction and end up—with their outer sliding elements 11*b*—against the outer sides of sliding rods 7, 8.

Upon a motion in the opposite direction, connecting rod 15 is displaced in distal direction. Now, sliding members 11, 12 come to abut with their inner sliding elements 11*a* at the inner sides of sliding rods 7, 8 and press these apart within the meaning of an opening motion of jaw pieces 5, 6.

It can be seen that both motions of the jaw pieces are brought about with the same force.

Preferably, the shown jaw instrument 1 is designed as bipolar forceps. Both jaw pieces 5, 6 are equipped with electrodes that are to be connected to different terminals of a power source.

In addition, FIG. 1 shows that jaw pieces 5, 6 are connected electrically via the electrically conductive sliding rods 7, 8.

In the case of jaw piece 5, the electric connection extends over sliding rod 7, joint 9, and end piece 10, all of which are electrically conductive metal parts. End piece 10 is, as shown in FIG. 1, fastened directly to metal tube 3, for example, via welding or soldering that is not shown. At the proximal end of shaft 2—not shown—the metal tube can be connected by a line 16 to a terminal of a power source that is not shown.

Jaw piece 6 is likewise electrically connected by its sliding rod 8, not, however to the metal tube 3, with which end piece 10 of sliding rod 8 is connected isolating by an adhesive connection 17. Rather, in this case, the electric connection takes place via the sliding contact with sliding member 12, which is connected by the electrically conductive connecting rod 15 and a sliding contact 18 to an electric line 19 that extends to the second terminal of a power source that is not shown. To avoid a short circuit between the two terminals, cross piece 13 is connected with sliding member 11 by an isolator 20.

FIGS. 2 and 3 show embodiment variants of sliding bodies 11, 12 of FIG. 1. Sliding member 21 of FIG. 2 differs from sliding member 11 of FIG. 1 thereby, that the two diametrically opposed sliding elements 21*a* and 21*b* that are designated for sliding contact with sliding rod 7, are not designed as sharp cutting blades according to FIG. 1, but as rounded surfaces.

Sliding member 31 of FIG. 3 has much broader, flat contact surfaces 32 with which attachment is possible in a large area at sliding rod 7. As a result, the forces that are to be transmitted can be introduced in a large area and a safe electric contact can also be achieved.

FIG. 4 shows an embodiment variant of the design shown in FIG. 1, which is shown highly simplified. To the extent possible, the same reference numbers as those in FIG. 1 are used.

In jaw instrument 41 that is shown here, the jaw parts 5, 6 are connected with their pertaining sliding rods 7, 8 by curved pieces 42, 43. Curved pieces 42, 43 are respectively mounted in a groove that is delimited by concentric surfaces. Between curved pieces 42 and 43, the groove is delimited by the outer surface of a pin 44. The outer groove surfaces are formed by retaining pieces 45 and 46. Pin 44 and retaining pieces 45 and 46 are fastened at the shaft, which is shown only with metal tube 3 in FIG. 4.

The pivoting operation of sliding rods 7, 8 takes place with sliding members 11 and 12 in the design in FIG. 1, which are correspondingly connected with connecting rod 15.

Jaw piece 5 and sliding rod 7 form a two-armed lever that is connected by curved piece 42, just like jaw piece 6 is connected with sliding rod 8 by curved piece 43. These two two-armed levers can be deviated around the axis of deviation extending in the center of pin 44 perpendicular to the plane of projection, whereby the curved pieces 42 and 43 run against the outer surface of pin 44 with their inner surface, and the outer sides of curved pieces 42 and 43 are retained against pin 44 by the abutting concentric surfaces of retaining pieces 45 and 46.

Thereby, a pivoting bearing of jaw pieces 5, 6 results with pivoting drive via sliding rods 7, 8 that operates, in the final analysis, just like in the embodiment in FIG. 1. Only the direction of motion is the reverse. As the arrows in FIG. 4 show, jaw 5, 6 is closed when connecting rod 15 is displaced in distal direction. Even in this design, a high degree of force can be applied in the direction of opening as well as in the direction of closing.

Even the design of FIG. 4 can be equipped with electric load of jaw pieces 5, 6, whereby here, particularly simple design relationships result. The details of the electric connection are not shown in FIG. 4. For such, many possibilities exist.

Thus, for example, one of the jaw pieces 5, 6 can be connected by one of retention pieces 45, 46 in sliding contact. The other jaw piece can then, for example, be connected by pin 44 or by the other retention piece.

One or both jaw pieces can also be connected via sliding elements 11 or 12 and connecting rod 15.

The goal of the previously described types of the electric contact of jaw pieces 5 and 6 with the aid of FIGS. 1 and 4 is, to use, if possible, the available mechanical structures as electric conductors extending over the length of shaft 2, i.e. metal tube 3, for example, and connecting rod 15. However, simpler types of contact are also possible, whereby, for example, in the design of FIG. 1, both end pieces 10 are connected isolating with an adhesive connection 17, and are contacted with isolated electric cables—not shown—that run through tube 3 and are connected to lines 16 and 19.

Jaw pieces 5, 6 that are shown in FIGS. 1 and 4 can, as illustrated, be the jaw pieces of a forceps, but in a somewhat different execution of the design, also be the cutting blades of a scissors. Even when designed as scissors, a bipolar electric connection would be advantageous.

What is claimed is:

1. A surgical jaw instrument comprising:

two jaw pieces mounted on a distal end section of a shaft, at least one of the jaw pieces being movable relative to the other jaw piece;

a sliding rod fastened at each movable jaw piece, the sliding rod at each movable jaw piece being inclined with respect to an axis of the shaft and being provided with:

a first sliding element displaceable parallel to the axis of the shaft that slidably engages the sliding rod in such a way that, upon a displacement of the first sliding element, the jaw pieces are relatively displaced; and a second sliding element that slidably engages the sliding rod and is fastened to the first sliding element diametrically opposed relative to the sliding rod.

2. A surgical jaw instrument as recited in claim 1, wherein an end of each sliding rod, opposite to the sliding rods' respective jaw piece, is fastened with a joint to the shaft.

3. A surgical jaw instrument as recited in claim 2, wherein the joint is a bendable part of the sliding rod.

4. A surgical jaw instrument as recited in claim 1, wherein each sliding rod is connected with the respective jaw piece by a bearing component that is rotatably mounted for rotation around a bearing axis, the bearing axis being aligned transverse to the axis of the shaft.

5. A surgical jaw instrument as recited in claim 4, wherein the bearing component is a curved piece extending concentric to the bearing axis, which deflects in a groove that is formed between two curved surfaces, the two curved surfaces are fastened at the shaft and extend concentric to the bearing axis.

6. A surgical jaw instrument as recited in claim 1, wherein at least one of the jaw pieces is provided with an electrode that is electrically connected by the sliding rod fastened to the at least one jaw piece.

7. A surgical jaw instrument as recited in claim 6, wherein both jaw pieces are provided with electrodes, one jaw piece is electrically connected via the shaft, the other jaw piece is electrically connected via one of the first sliding element or the second sliding element that abuts at the sliding rod, and a connecting rod driving the sliding elements.

8. A surgical jaw instrument as recited in claim 1, wherein the first and second sliding elements engage the sliding rod in a direction parallel to a plane of a jaw movement.

9. A surgical jaw instrument as recited in claim 1, wherein each of the two jaw pieces is movable relative to the other jaw piece.

* * * * *